United States Patent
Potthoff et al.

(10) Patent No.: US 9,493,407 B2
(45) Date of Patent: Nov. 15, 2016

(54) UREA GRANULATION PROCESS WITH SCRUBBING SYSTEM

(71) Applicants: Matthias Potthoff, Dortmund (DE); Harald Franzrahe, Dortmund (DE); Luc Albert Vanmarcke, Lembecke (BE)

(72) Inventors: Matthias Potthoff, Dortmund (DE); Harald Franzrahe, Dortmund (DE); Luc Albert Vanmarcke, Lembecke (BE)

(73) Assignee: UHDE FERTILIZER TECHNOLOGY B.V., NW Roermond (NL)

( * ) Notice: Subject to any disclaimer, the term of this patent is extended or adjusted under 35 U.S.C. 154(b) by 0 days.

(21) Appl. No.: 14/399,473

(22) PCT Filed: May 2, 2013

(86) PCT No.: PCT/EP2013/001292
§ 371 (c)(1),
(2) Date: Nov. 6, 2014

(87) PCT Pub. No.: WO2013/167245
PCT Pub. Date: Nov. 14, 2013

(65) Prior Publication Data
US 2015/0133689 A1 May 14, 2015

(30) Foreign Application Priority Data

May 8, 2012 (EP) .................................. 12003585

(51) Int. Cl.
| | | |
|---|---|---|
| *C07C 273/02* | (2006.01) | |
| *C05C 9/00* | (2006.01) | |
| *C05C 9/02* | (2006.01) | |
| *C07C 273/16* | (2006.01) | |
| *B01D 53/58* | (2006.01) | |
| *B01J 2/00* | (2006.01) | |

(52) U.S. Cl.
CPC ............ *C07C 273/02* (2013.01); *B01D 53/58* (2013.01); *B01J 2/00* (2013.01); *C05C 9/005* (2013.01); *C05C 9/02* (2013.01); *C07C 273/16* (2013.01); *B01D 2258/02* (2013.01)

(58) Field of Classification Search
CPC .................. C07C 273/02; C07C 273/16; C05C 9/005; C05C 9/02
See application file for complete search history.

(56) References Cited

U.S. PATENT DOCUMENTS

| | | | | |
|---|---|---|---|---|
| 4,120,685 | A | * | 10/1978 | Vargiu ...................... C05C 9/02 564/60 |
| 4,370,198 | A | | 1/1983 | Dencs et al. |
| 4,507,129 | A | | 3/1985 | Storen |
| 5,686,647 | A | * | 11/1997 | Chys ..................... C07C 273/04 504/327 |
| 5,779,945 | A | | | 7/1998 Nijsten et al. |
| 2007/0039469 | A1 | | 2/2007 | Niehues et al. |
| 2011/0091369 | A1 | | 4/2011 | Casara et al. |
| 2012/0039787 | A1 | | 2/2012 | Casara et al. |

FOREIGN PATENT DOCUMENTS

| | | | |
|---|---|---|---|
| EP | 0853971 A1 | 7/1998 | |
| JP | 2000001466 A | 1/2000 | |
| JP | 2000279736 A | 10/2000 | |
| WO | 03/099721 A1 | 12/2003 | |
| WO | 2010/060535 A1 | 6/2010 | |
| WO | WO 2010060535 A1 * | 6/2010 | ............ C05C 3/005 |

OTHER PUBLICATIONS

International Search Report for International patent application No. PCT/EP2013/001292; mailing date Sep. 23, 2013.
Written Opinion of the International Search Authority for International patent application No. PCT/EP2013/001292; mailing date Sep. 23, 2013.
Anonymous: "Injectors remove dust from gas stream in urea plant", Spraying Systems, Oct. 15, 2010 (Oct. 15, 2010), XP002695749, Retrieved from the Internet: URL:http://www.spray.com/literature_pdfs/CS116_Ammonia_Abatement_Urea_Plant.pdf.
Potthoff, M. "Innovative Ammonia Emisssion Reductions," Nitrogen + Syngas, [online], Jul./Aug. 2008, pp. 39-41. URL: http://www.uhde-fertilizer-technology.com/fileadmin/Userfiles/2008-Jul-Aug_nitrogen_syngas.pdf.
English translation of Abstract of JP 2000279736 A, Oct. 10, 2010.
English translation of Abstract of JP 2000001466 A, Jan. 7, 2000.

* cited by examiner

*Primary Examiner* — Sudhakar Katakam
(74) *Attorney, Agent, or Firm* — thyssenkrupp North America, Inc.

(57) ABSTRACT

Disclosed is a method for producing granular urea and reducing ammonia emissions in a gaseous waste stream of the urea granulation process. The method includes the steps of granulating urea and generating a gaseous waste stream from the granulation of the urea, first washing the waste stream in a first scrubber dust stage to remove dust form the gaseous waste stream, and then reacting the gaseous waste stream with formaldehyde in a formaldehyde stage to generate a hexamethylenetetramine and urea-formaldehyde liquid stream, and an ammonia-reduced off-gas stream.

15 Claims, 3 Drawing Sheets

US 9,493,407 B2

UREA GRANULATION PROCESS WITH SCRUBBING SYSTEM

CROSS REFERENCE TO RELATED APPLICATIONS

This application is a U.S. National Stage Entry of International Patent Application Serial Number PCT/EP2013/001292, filed May 2, 2013, which claims priority to European patent application no. 12003585.2, filed May 8, 2012.

FIELD

The invention relates to a urea granulation process and to the apparatus suitable for operating such a process. The invention integrates a method for reducing ammonia emissions from a urea granulation plant which is currently emitted by a conventional urea production process by scrubbing the off-gas. The scrubbing system bears the advantage that the amount of ammonia in off-gas can be reduced and in addition the generation of ammonium salts can be reduced.

BACKGROUND

A common process for producing granules from a liquid composition is described in U.S. Pat. No. 5,779,945. The focus of U.S. Pat. No. 5,779,945 is the treatment and sorting of generated granules with different sizes. Herein a gas/solids separating apparatus such as a cyclone or a scrubber is used to separate solid material from the off-gas stream of the apparatus. Advanced treatment of the off-gas stream is not taken into further account.

In U.S. Pat. No. 4,370,198 the off-gas of the granulation unit is sent to a dust separation cyclone followed by a continuous wet scrubber which both contributes to the scrubbing off said off-gas stream. The scrubbing liquid used is part of the solution or suspension to be proceeded and the scrubbing liquid leaving the wet scrubber is fed back directly into the granulation unit. Exemplarily, the described process can be achieved for the production of sodium chloride, urea, saccharose or ferric oxide, respectively. Hereby the scrubbing liquor is part of the solution or suspension to be processed and is send directly back into the granulation unit. This process can be only achieved for dust scrubbing but is not suitable for ammonia scrubbing.

A further example for an apparatus and a method for wet type simultaneous cleaning and dust-removing gas treatment in a horizontal cross-flow scrubber are disclosed in EP 0853971 A1. This invention performs the removal of pollutants and dust in a packed tower.

In a urea plant used air exiting a urea granulator that is equipped with a fluidized bed contains in addition to urea dust also ammonia. This ammonia contamination needs to be removed before the off-gas stream can be vented into the atmosphere.

Removing ammonia from an off-gas stream is a well-known technology. Usually the off-gas stream is treated with an acidic scrubbing solution. This scrubbing solution can be easily manufactured by adding an acid such as nitric acid or sulphuric acid to water. The ammonia is removed from the gas stream by chemical absorption and converted to the corresponding ammonium salt. The use of nitric acid produces ammonium nitrate (AN), and the use of sulphuric acid produces ammonium sulphate (AS) respectively. These ammonium salt-containing solutions can be used for the production of ammonium sulphate fertilizer or NPK fertilizer, the technology for this is state of the art.

In a urea plant, ammonium salts do not occur in the process and cannot easily be processed at existing urea facilities. A conventional urea production facility therefore has only the following options to reduce gaseous ammonia emissions from the granulation plant:
- to discharge the diluted ammonium salt solution to a waste water stream,
- to concentrate the diluted ammonium salt solution up to a concentration which can be utilized by other plants, e.g. NPK,
- to produce UAS (urea/ammonium sulphate) fertilizer with a high sulphur content,
- to produce UAN (urea/ammonium nitrate) solution.

All of these alternatives require significant investments and changes to operating conditions or entail changes of the product composition and characteristics. All above options result in new products that require additional facilities for transport and handling as well as energy utilities in expensive quantities. As a consequence, nowadays, urea facilities are run without efficient ammonia removal causing severe environmental problems. Therefore, ammonia removal from a urea facility is a challenging task that needs to be solved.

An alternative solution is described in WO 03/099721. This invention relates to a process for removing ammonia from an ammonia-containing gas stream by converting the ammonia in the ammonia-containing gas stream with an organic acid into an ammonium salt, whereas the obtained ammonium salt is contacted, at elevated temperature, with peroxide. The ammonium salt is hereby converted into a $NH_3$, $CO_2$ and $H_2O$ containing mixture in a decomposer and can readily be reprocessed in a urea synthesis unit. The peroxide is supplementary to the common process and may relate to other negative accompaniments. Also, for the conversion of the ammonium salt into $NH_3$, $CO_2$ and $H_2O$ a separate decomposer in addition to the normal plant layout is required. This emerging gas stream can not be reprocessed in a granulation unit but needs to be recycled in a urea synthesis unit.

Reductions of ammonia emissions are also described in M Potthoff, Nitrogen+Syngas, [online], July. August 2008, pages 39-41. In FIG. 1 a combined dust and acidic scrubber system is shown. The ammonia is absorbed in the acidic scrubbing section and converted into ammonium sulphate. The ammonium sulphate solution is added to the recycle flow going back to the evaporation section. In this unit it is mixed with urea melt from the urea synthesis unit. The concentrated liquor stream from the evaporation is conveyed into the urea granulator. The condensate coming out of the evaporation unit is utilised as makeup for the combined dust/ammonia scrubbing system. With this so called Ammonia Convert Technology ammonia in off-gas can be reduced to 30 mg/Nm$^3$. The technology without acidic scrubbing as shown in Brochure Urea, [online], 12-2007, pages 1-24 reduces ammonia in off-gas only to values of around 160 mg/m$^3$.

The ammonia convert technology described in M Potthoff, Nitrogen+Syngas, [online], July. August 2008, pages 39-41 implicates still several disadvantages. First of all, the water balance in this system is a critical parameter. If disturbed, urea synthesis will be contaminated with ammonium sulphate or alternatively large amounts of waste water need to be treated. In addition, mixing of acidic solution with concentrated urea melt in the evaporation unit has adverse effects on granulation. Moreover, this technology implicates the generation of large amounts of condensate contaminated with ammonium sulphate that needs to be distributed to various scrubbers, including dust and acidic scrubbing technology. Also the remaining ammonia concentration in the off-gas achieved with this technology is still not sufficient or satisfactory for modern urea granulation plants.

In WO 2010/060535 A1 the ammonia convert technology described in M Potthoff, Nitrogen+Syngas, [online], July. August 2008, pages 39-41 is improved in order to achieve ammonia concentrations in off-gas of 10 mg/Nm$^3$. WO 2010/060535 A1 teaches that a scrubber dust stage, that is connected to process coolers, is operated through an ammonium salt solution stream generated in a scrubber acid stage, which is connected to the urea granulator. Therefore the scrubbing system presented in WO 2010/060535 A1 represents an in itself complete closed system as described in the characteristic part of claim 1 of this invention. This technology avoids contamination of the urea melt generated in the urea synthesis unit by building such a complete closed scrubbing system. The disadvantage of this system is that it is very complex in its performance.

In U.S. Pat. No. 5,686,647 a process for preparing urea is described wherein an amount of formaldehyde is added to an off-gas stream containing gaseous ammonia to form hexamethylenetetramine, which is returned into the process before the granulation step. This formaldehyde addition can be performed before or during a washing step with liquid urea solution whereby this washing step serves as dust scrubbing device. The disadvantage of this technology is the relatively high amount of ammonia in the off-gas of circa 90 mg/Nm$^3$ in comparison to the technology presented in WO 2010/060535 A1.

SUMMARY

An object of the present disclosure is to provide a process which integrates and optimizes technology for scrubbing off-gas generated by a urea granulation process. The process eliminates problems associated with the use of conventional technologies as described above, and should be easy to integrate into current state of the art scrubbing systems. It is also an object of the present disclosure to provide an apparatus suitable to perform such a process.

BRIEF DESCRIPTION OF THE DRAWINGS

The present invention is described in detail below with reference to the attached drawing figures, wherein.

DETAILED DESCRIPTION

Figure 1:
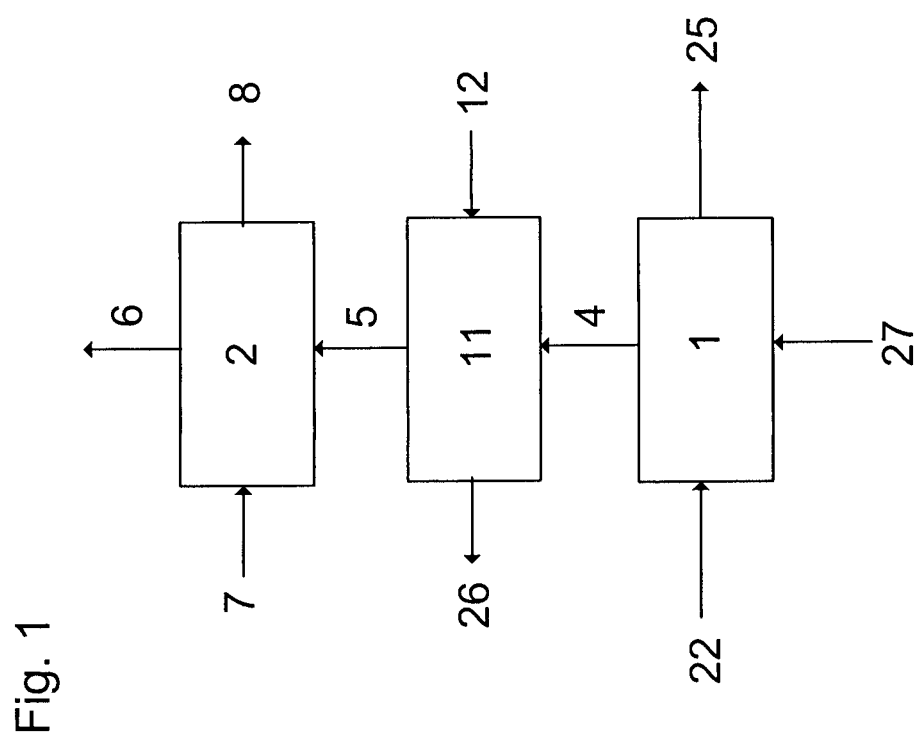
FIG. 1 is a schematic block, diagram of an embodiment of a urea granulation process utilizing an ammonia formaldehyde convert process, as disclosed herein.

This is achieved by a urea granulation process with scrubbing system including at least one gaseous waste stream for removal of dust and ammonia whereby this waste stream is processed through a combination of the following process steps comprising (a) washing the dust and ammonia laden stream 4 with water and/or an aqueous urea solution whereby a dust-laden liquid stream 26 and a dust-reduced stream 5 is generated, and (b) reacting the dust-reduced stream 5 with formaldehyde 7 to form a stream comprising hexamethylenetetramine and urea-formaldehyde 8 and clean off-gas 6 wherein the gas stream is directed first through process step (a) and then through process step (b).

Surprisingly the sequence of process steps in the above disclosed embodiment of a method of the present disclosure permits the further reduction of ammonia emissions form granulation plants in comparison to the technology described in U.S. Pat. No. 5,686,647, in which the order of process steps is reversed. If process step (b) is done before the dust scrubbing in process step (a) the reaction ammonia-formaldehyde suffers from competition with the standard urea-formaldehyde reaction which would prevail in the dilute urea solution obtained in the scrubber. Therefore efficiency in this process step is lost and ammonia-reduction is limited.

Hereby the urea concentration of the dust-laden liquid stream 26 is kept in a range from 35 to 60% wt, and preferably is kept in a range from 45 to 55% wt and that dust laden liquid stream 26 is returned into the process before the granulation step.

Furthermore 70 to 90 wt % of ammonia in relation to the total ammonia content of the dust-reduced stream 5 is reacted to hexamethylenetetramine in the formaldehyde stage 2.

Optionally, the stream comprising hexamethylenetetramine and urea-formaldehyde 8 is returned into the process before the granulation step. The hexamethylenetetramine comprises urea-formaldehyde solution and therefore replaces at least part of the urea/formaldehyde solution normally used as granulation additive.

In a further embodiment of the current process the dust-laden liquid stream 26 is mixed with the stream comprising hexamethylenetetramine and urea-formaldehyde 8 before returning this mixture into the process before the granulation step.

In a further embodiment of the invention an additional process step for removing ammonia is implemented downstream of process step (b) wherein an ammonia-laden stream is brought into contact with an acid 9 in liquid phase and thereby ammonia is scrubbed from that stream by the generation of an ammonium salt stream 10 in a scrubber acid stage 3.

The combination of these three process steps bears the advantage that the amount of ammonium salt generated in the scrubber acid stage 3 is greatly reduced so that these salts do not disturb the granulation system or the urea synthesis system if recycled back in one of these systems. Also the amount of ammonia reduced by this system can be improved.

Hereby 94 to 99.9% of ammonia in relation to the total ammonia content of the dust- and ammonia-laden stream 4 is eliminated through the combination of process steps (a) and (b) with a further acidic treatment.

In an embodiment of the invention the acid is selected from the group consisting of sulphuric acid, nitric acid, phosphoric acid, citric acid, lactic acid and oxalic acid. Other acids can be used if they are non-volatile. Preferably, sulphuric acid is used, as it is readily available and in addition, it supplies sulphur which is considered to be a highly demanded nutrient.

Furthermore the ammonia salt concentration of the ammonium salt stream generated in the scrubber acid stage is kept <40% wt, and preferably is kept in a range from 35-40% wt.

The pH of the ammonia salt stream generated in the granulator scrubber acid stage is kept in a range from 2-6, and preferably is kept in a range from 3.5-5.0, and most preferably is kept in a range from 4.0-4.5.

In an optional embodiment a second gaseous dust- and ammonia-laden stream 14 drawn off from product coolers 13 is generated, which stream is send through a further scrubber dust stage 15 in which the ammonium salt stream 10 of the further acid treatment is used to remove the ammonia from this second gaseous dust- and ammonia-ladden stream 14.

In a further optional embodiment of the current invention the scrubbing system being passed is in itself a complete closed system, whereby the ammonium salt stream 10 from the scrubber acid stage 3 is fed into said further scrubber dust stage 15, and the released solution 17 from said further scrubber dust stage 15 is send to a evaporation unit 16, the vapour stream 18 from the evaporation unit 16, which contains ammonia is given into a condenser unit 19, which releases a liquid process condensate 20, and said liquid process condensate 20 is given into the scrubber acid stage 3, and the concentrated liquor stream 21 generated in the evaporation unit 16, containing urea and ammonium salt, and a urea melt 22 is conveyed into the urea granulator 1.

Hereby the scrubbing system in itself is a complete closed system, and is therefore totally decoupled from urea synthesis. Thereby contaminations of the urea melt are totally avoided.

With advantage the concentration of the urea melt 22 and concentrated liquor stream 21, containing urea and ammonium salt, for the urea granulator being kept in a range from 95 to 99.8% wt, and being preferably kept in a range from 96 to 97.5% wt.

Optionally a portion of urea melt 22 is fed into the evaporation unit 16.

Furthermore the clean off-gas 6 is released into the atmosphere and exhibits a concentration of $NH_3$ in the range of 5-30 $mg/Nm^3$, and preferably exhibits a concentration of $NH_3$ being <10 $mg/Nm^3$.

The current invention also comprises an apparatus with scrubbing system system including at least one gaseous waste stream for the removal of dust and ammonia comprising a scrubber dust stage 11, in which dust is washed off from a dust- and ammonia-ladden stream, and a formaldehyde stage 2, in which part of the ammonia of the ammonia-ladden air 4 is reacted with formaldehyde 7 to form hexamethylenetetramine, whereby the scrubber dust stage 11 is arranged upstream of the formaldehyde stage 2.

Furthermore an additional scrubber acid stage 3 is integrated into the scrubbing system downstream of the formaldehyde stage 2.

Optionally the urea granulation apparatus with scrubbing system comprises also product coolers 13, in which a second gaseous ammonia-laden stream 14 is generated, and which product coolers 13 are connected with a further scrubber dust stage 15 which is connected with means for conveying the ammonium salt solution stream 10 from the scrubber acid stage 3 to said further scrubber dust stage 15.

In a further embodiment of the urea granulation apparatus the apparatuses of the scrubbing system being connected in such a way that a complete closed system of waste streams is built, comprising means for conveying the ammonium salt stream 10 from the scrubber acid stage 3 to the further scrubber dust stage 10, and means for conveying the solution 17 from said further scrubber dust stage 15 to an evaporation unit 16, means for conveying the steam vapour 18 of the evaporation unit 16 to a condenser unit 19, means for conveying the process condensate 20 from the condenser unit 19 to the granulator scrubber acid stage 3, and means for conveying urea melt 22 and a means for conveying a concentrated liquor stream 21, containing urea and ammonium salt into the urea granulator 1.

Furthermore the apparatus comprises means for conveying a portion of urea melt to the evaporation unit 16.

With advantage scrubbers used in the current technology are horizontal scrubbers.

FIG. 1 shows an urea granulator 1, which is supplied with urea melt or an aqueous urea solution 22. In the urea granulator 1 urea granules are formed in a fluidized bed, which is fluidized by an air stream 27. A dust- and ammonia-laden stream 4 is drawn off. It is first scrubbed in the scrubber dust stage 11, where urea dust is removed. A stream of process water or diluted urea solution 12 is added to the scrubber dust stage 11 and the dust-laden stream 26 is drawn-off from the scrubber dust stage 11. The dust-reduced stream 5 is then sent to the formaldehyde stage 2. According to the invention formaldehyde 7 is introduced in the formaldehyde stage 2. A hexamethylenetetramine and formaldehyde containing stream 8 is drawn-off from the formaldehyde stage 2. This hexamethylenetetramine can be returned into the granulation process before the granulation step. The clean off-gas 6 is send into the atmosphere.

Figure 2:
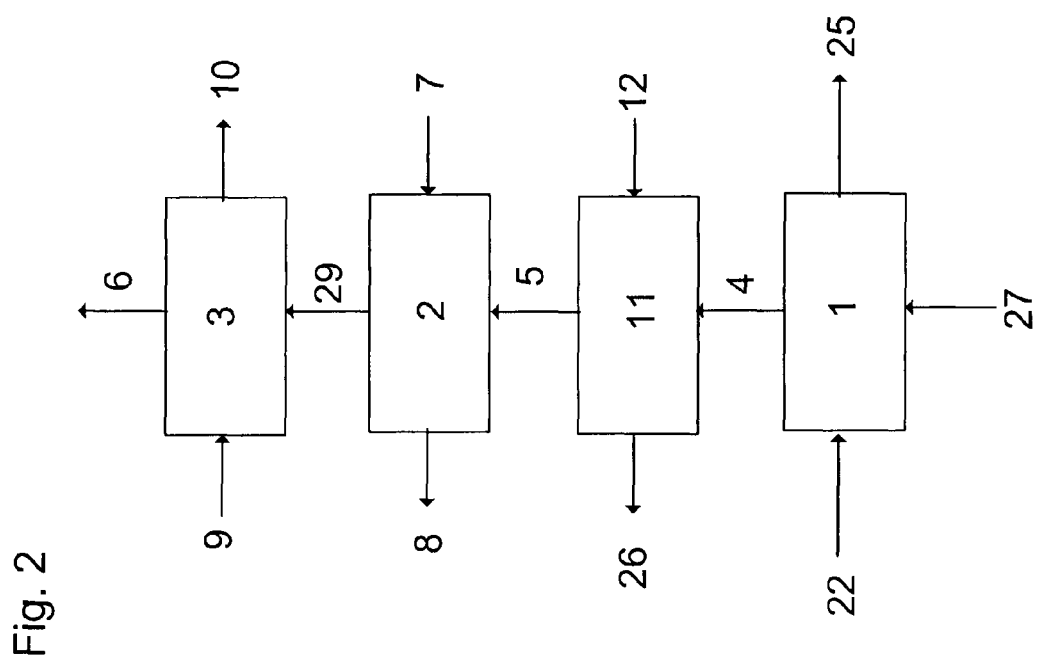
FIG. 2 is a schematic block diagram of an embodiment of a urea granulation process utilizing an ammonia formaldehyde convert process, including a scrubber acid stage, as disclosed herein.

FIG. 2 includes in comparison to FIG. 1 an additional scrubber acid stage 3 downstream of the formaldehyde stage 2. The ammonia reduced stream 29 from the formaldehyde stage 2 is send into the scrubber acid stage 3 where the rest of ammonia is removed, and the clean off-gas stream 6 can be drawn off. The scrubbing solution for the scrubber acid stage 3 consists of process water and the acid 9 in liquid phase. In the granulator scrubber acid stage 3 the acid solution reacts with ammonia producing an ammonium salt stream 10. This ammonium salt stream 10 can be further processed as shown in FIG. 3 or can be drawn-off from the urea granulation system.

This inventive process allows the reduction of ammonium salts generated in the scrubber acid stage 3 but is very effective in reducing ammonia emissions from urea granulation plants. Ammonium salts are much undesired because they cause severe environmental problems and cause problems in urea granule quality if added to high concentrations to the granulation process.

Figure 3:
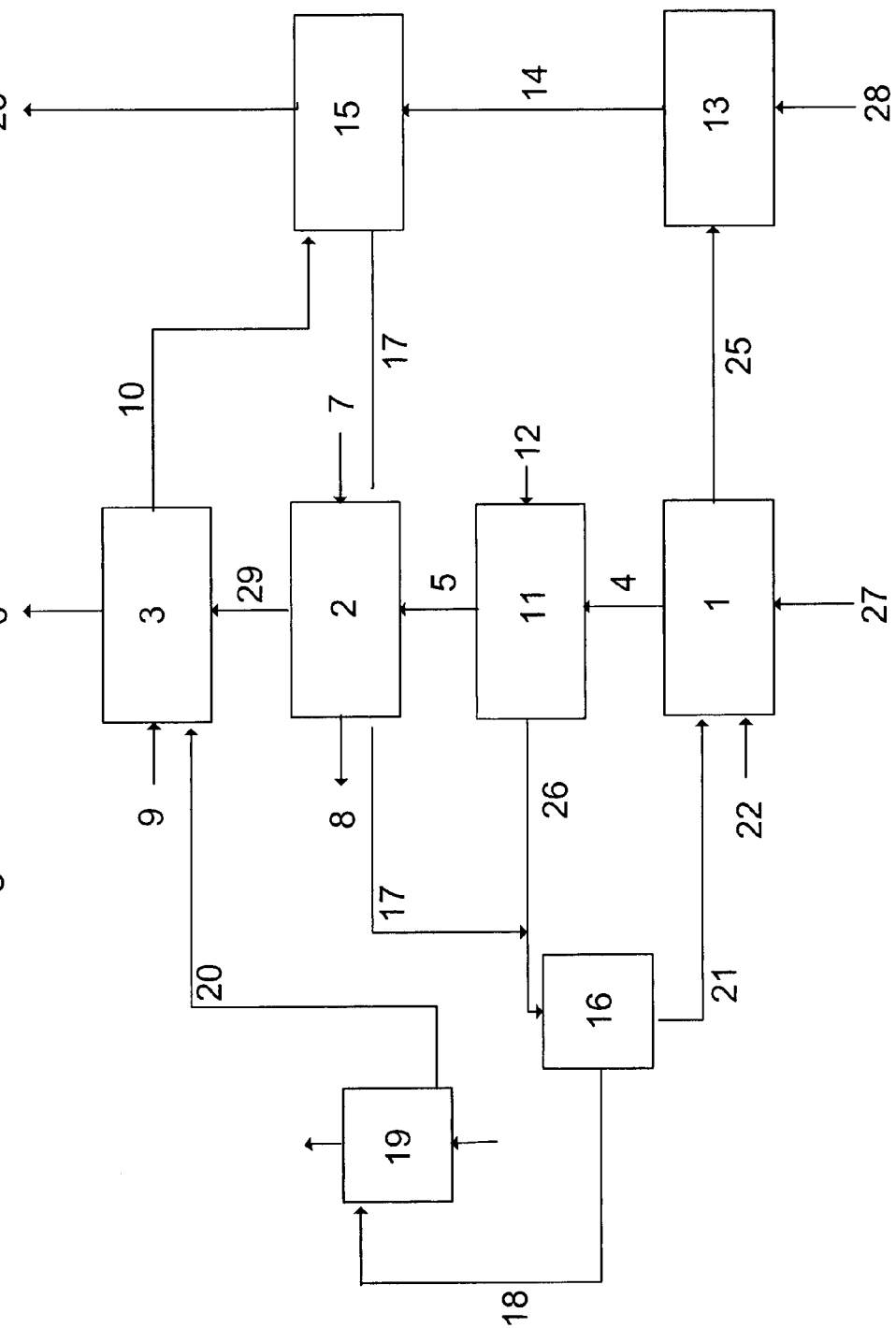
FIG. 3 is a schematic block diagram of an embodiment of a urea granulation process including a closed scrubbing system, as disclosed herein.

FIG. 3 includes in comparison to FIG. 2 a in itself closed scrubbing system including the inventive process steps. In addition to FIG. 2 product coolers 13 are shown, in which the hot granules 25 produced are conveyed. Air 28 cools the final product 25. The dust-laden air stream 14 is conveyed to a further scrubber dust stage 15, where the urea dust is washed out while the air is cooled down by evaporation of water in the scrubber. The clean off-gas 23 leaving the scrubber dust stage 15 is to the atmosphere.

The resulting solution 17 from the scrubber dust stage 15, is combined with the dust-laden stream 26 from the granulator scrubber dust stage 11 and the resulting mixture is conveyed to the evaporation unit 16, where it is concentrated. The concentrated liquor stream 21 from the evaporation unit 16 is fed to the urea granulator 1 to integrate the generated ammonium salt into the granulation process. A portion of the urea melt 22 can be added to the evaporation unit 16 (not shown), in order to keep the urea concentration and the ammonium sulphate concentration of the concentrated liquor stream 21 in the right ratio. The steam vapour 18 drawn off from the evaporation unit 16 is conveyed to a condenser unit 19, where it is cooled by external cooling water. The liquid process condensate 20 generated during the condensation is send into the scrubber acid stage 3. To close the scrubbing cycle the ammonium salt stream 10 drawn-off from the scrubber acid stage 3 is send to the scrubber dust stage 15.

Therefore a closed circle of waste streams is formed and all waste streams are recycled. In addition the generated ammonium salts are integrated in the urea granulation process. Also external process water consumption is reduced to a minimum. Altogether, this combination is characterized by its environmental compatibility. Also the content of ammonium salt in the generated urea granules is reduced, which gets problematic if sulphuric acid is used as acid 9 and the sulphur content of the granules increase.

Example 1

In example 1 a table is shown giving some typical figures concerning ammonia in the urea granulation processes state of the art as described in Brochure Uhde, Urea, [online] 2011 compared with a formaldehyde treatment as described in U.S. Pat. No. 5,686,647 implemented before or combined with a scrubber dust stage and the inventive technology:

In a urea granulation process with formaldehyde scrubbing a formaldehyde-containing solution is added to the ammonia-laden air or the formaldehyde stage.

The formaldehyde-containing solution used for scrubbing is charged with hexamethylenetetramine and is partially reintroduced into the above described urea process. Basically this mixture after being brought to the right pressure and temperature may be recycled in every phase of the process.

The amount of ammonia of 500 to 600 ppm by weight in the feed to the granulation unit is more or less unavoidable as it is the result of the equilibrium formed in an upstream to the granulation unit arranged evaporation unit, if the concentrated liquor stream generated in this evaporation unit shall be introduced into the granulator. About 90 ppm ammonia is added through biuret formation in the urea solution, which is fed into the granulator, so that in total about 590 to 690 ppm enters the granulation unit. About 50 ppm of this ammonia is included in the final product, whereby the rest leaves the granulation plant with the air flow from the granulation unit via stacks. This results in a final concentration of approximately 130 to 160 mg/Nm$^3$ for the technology state of the art as presented in Brochure Urea, [online], 2011. In the technology described by U.S. Pat. No. 5,686,647 a final concentration of circa 86 mg/Nm$^3$ can be reached. If formaldehyde stage is put into practice after a dust scrubber where the urea is almost removed, as the current invention shown in FIG. 1 suggests, a final concentration of approximately 30 mg/Nm$^3$ ammonia is found in a combined stack. The inventive technology in combination with a following acid scrubbing stage as shown in FIG. 2 can lead to ammonia concentrations of 10 mg/Nm$^3$ with a minor amount of acid to be used. Therefore a drastically improvement can be achieved using this technology.

TABLE 1 technology state of the art in comparison with current invention

| | technology state of the art (Brochure Urea, 2011) | formaldehyde treatment as described in U.S. Pat. No. 5,686,647 before a scrubber dust stage | formaldehyde treatment of the current invention as shown in FIG. 1 | Formaldehyde treatment of the current invention as shown in FIG. 2 |
|---|---|---|---|---|
| Free ammonia from evaporation unit | ≈500 to 600 ppm wt. | | | |
| Ammonia from biuret formation | ≈90 ppm wt. | | | |
| Total free ammonia at granulator inlet | ≈590 to 690 ppm wt. | | | |
| Free ammonia in final product | ≈50 ppm wt. | | | |
| Free ammonia released (based on urea solution) | ≈540 to 640 ppm wt. | | | |
| Ammonia - formaldhyde stage | none | yes | yes | yes |
| Dose Formaldehyde as UFC via 7 kg/ton | | 4 | 4 | 4 |
| Typical ammonia concentration in combined stack | ≈130 to 160 mg/Nm$^3$ ≅ 0.6 to 0.7 kg/ton$_{product}$ | ≈86 mg/Nm$^3$ ≅ 0.40 kg/ton$_{product}$ | ≈30 mg/Nm$^3$ ≅ 0.14 kg/ton$_{product}$ | ≈10 mg/Nm$^3$ ≅ 0.05 kg/ton$_{product}$ |

TABLE 1-continued technology state of the art in comparison with current invention

| | technology state of the art (Brochure Urea, 2011) | formaldehyde treatment as described in U.S. Pat. No. 5,686,647 before a scrubber dust stage | formaldehyde treatment of the current invention as shown in FIG. 1 | Formaldehyde treatment of the current invention as shown in FIG. 2 |
|---|---|---|---|---|
| Formaldehyde efficiency | | 45.00% | 75.00% | 75.00% |
| Ammonium sulphate produced | | | | ≅0.35 kg/ton$_{product}$ |

The efficiency of formaldehyde to abate ammonia is strongly reduced to only 45% if the process is done before the dust scrubbing. If it is done in combination with the dust scrubbing the formaldehyde efficiency is 75%. The reaction ammonia-formaldehyde suffers from competition with the standard urea-formaldehyde reaction which would prevail in the dilute urea solution obtained in the scrubber. Therefore the change in the sequence of process steps of the current invention in relation to the teaching of U.S. Pat. No. 5,686,647 has an enormous positive effect in respect to the ammonia content in off-gas. The combination shown in FIG. 2 of a scrubber acid stage downstream of the formaldehyde stage has the advantage that the ammonium salt stream generated has a very low ammonium salt concentration if compared with the technology state of the art of WO2010060535A1 (table 2) in which a formaldehyde stage is missing. Therefore this ammonium salt stream can be exported from the granulation system or can be further processed as shown in FIG. 3.

Example 2

In example 2 a table is shown giving some typical figures concerning ammonia in the urea granulation processes state of the art as described in WO2010060535A1, in which the ammonium salt stream generated is reintroduced into the granulation process, whereby a in itself complete closed system of scrubbing streams is built, compared with the inventive closed scrubber technology as shown in FIG. 3: In a urea granulation process with a scrubber system according to FIG. 3 a formaldehyde-containing solution is added via 7 to the formaldehyde stage 2. The formaldehyde-containing solution used for scrubbing in formaldehyde stage 2 is charged with hexamethylenetetramine and is partially reintroduced into the standard urea process. Basically this mixture after being brought to the right pressure and temperature may be recycled in every phase of the process.

TABLE 2 technology state of the art in comparison with current invention as shown in FIG. 3:

| | technology state of the art (Brochure Urea, 2011) | Ammonia convert technology WO2010060535 A1 | Inventive technology (FIG. 3) |
|---|---|---|---|
| Free ammonia from evaporation section | ≈500 to 600 ppm wt. | | |
| Ammonia from biuret formation | | ≈90 ppm wt. | |
| Total free ammonia at granulator inlet | | ≈590 to 690 ppm wt. | |
| Free ammonia in final product | | ≈50 ppm wt. | |
| Free ammonia released (based on urea solution) | | ≈540 to 640 ppm wt. | |
| Ammonia - formaldhyde stage | none | none | yes |
| Dose Formaldehyde as UFC via 7 kg/ton | | | 4 |
| Formaldehyde efficiency | | | 75.00% |
| Acid scrubber stage | none | yes | yes |
| Typical ammonia concentration in combined stack | ≈130 to 160 mg/Nm³ ≅ 0.6 to 0.7 kg/ton$_{product}$ | ≈10 mg/Nm³ ≅ 0.05 kg/ton$_{product}$ | ≈10 mg/Nm³ ≅ 0.05 kg/ton$_{product}$ |
| Sulphuric acid consumption | | ≅2.0 kg/ton$_{product}$ | ≅0.27 kg/ton$_{product}$ |
| Ammonium sulphate produced | | ≅2.3 kg/ton$_{product}$ | ≅0.35 kg/ton$_{product}$ |

Thus, a solution is produced which shows ammonia concentrations in off-gas that are comparable to those reached with the technology described in WO2010060535A1. But in addition a very low ammonium salt concentration, which is approx. 8 times less then the technology described in WO2010060535A1 is produced. Also the sulphuric acid consumption is 8 times lower which is a significant cost reduction. There is no significant change to the product specification and quality by the addition of these small amounts of ammonium salts. The N content of the urea product stays above 46% N, so that the product is still a typical urea fertilizer.

The advantages of the proposed process are:
Significant low ammonia emissions to the environment.
Urea granule with very low ammonium salt concentration
Cost benefits are achieved by reducing the ammonia and acid consumption

- A simple way is used to process ammonia-laden gas streams in existing urea granulation plants.
- A proven and low-cost technical process is used to remove ammonia from the off-gas streams from the urea granulation plant with fluidized bed granulation.
- As the recovered ammonia is included in the product the urea production is increased, leading to a significant economic benefit.
- A typical urea fertilizer grade product is produced.

The invention claimed is:

1. A method for reducing ammonia emissions in a gaseous waste stream of a process for producing granular urea, comprising:
   granulating urea by the operation of a urea granulator;
   generating a dust and ammonia laden gaseous waste stream by the operation of the urea granulator;
   washing, in a first scrubber dust stage, the gaseous waste stream with at least one of water or an aqueous urea solution to generate a dust-laden liquid stream and a dust-reduced gas stream;
   after said washing step, reacting, in a formaldehyde stage, the dust-reduced gas stream with formaldehyde to generate a hexamethylenetetramine and urea-formaldehyde liquid stream, and an ammonia-reduced off-gas stream.

2. The method of claim 1, wherein a urea concentration of the dust-laden liquid stream is between about 35% wt to about 60% wt, the method further comprising returning the dust laden liquid stream into the urea granulation process before the granulating step.

3. The method of claim 1, wherein between about 70% wt to about 90% wt of ammonia, in relation to the total ammonia content of the dust-reduced gas stream, is reacted to hexamethylenetetramine in the formaldehyde reacting step.

4. The method of claim 1, further comprising returning the hexamethylenetetramine and urea-formaldehyde liquid stream into the urea granulation process before the granulating step.

5. The method of claim 1, further comprising:
   mixing the dust-laden liquid stream with the hexamethylenetetramine and urea-formaldehyde liquid stream;
   returning the mixed dust-laden liquid stream and hexamethylenetetramine and urea-formaldehyde liquid stream into the urea granulation process prior to the granulating step.

6. The method of claim 1, further comprising contacting, in a scrubber acid stage, the ammonia reduced off-gas stream with a liquid acid so as to scrub additional ammonia from the ammonia reduced off-gas stream by the generation of a resulting ammonium salt stream.

7. The method of claim 6, wherein between about 94% to about 99.9% of ammonia, in relation to the total ammonia content of the dust and ammonia laden gaseous waste stream, is eliminated following the contacting step of the scrubber acid stage.

8. The method of claim 6, wherein the liquid acid is selected from the group consisting of sulphuric acid, nitric acid, phosphoric acid, citric acid, lactic acid and oxalic acid.

9. The method of claim 6, wherein a concentration of ammonia salt in the ammonium salt stream is less than or equal to 40% wt.

10. The method of claim 6, wherein a pH of the ammonia salt stream is between about 2 and about 6.

11. The method of claim 6, further comprising:
    conveying granulated urea product from the urea granulator to a product cooler;
    generating a second dust and ammonia laden gaseous waste stream by the operation of the product cooler;
    in a second scrubber dust stage, washing the second dust and ammonia laden gaseous waste stream generated by the product cooler with the ammonium salt stream generated by the scrubber acid stage, so as to remove ammonia from the second dust and ammonia laden gaseous waste stream.

12. The method of claim 6, wherein one or more of said method steps are operated in a closed system, the method further comprising:
    feeding the ammonium salt stream from the scrubber acid stage into the second scrubber dust stage to generate a released solution;
    sending the released solution generated by the second scrubber dust stage into an evaporation unit to generate both:
       a vapor stream containing ammonia, and
       a concentrated liquor stream containing urea and ammonium salt;
    conveying the vapor stream generated by the evaporation unit to a condenser unit to generate a liquid process condensate;
    transferring the liquid process condensate to the scrubber acid stage; and
    conveying a urea melt and the concentrated liquor stream generated by the evaporation unit into the urea granulator.

13. The method of claim 12, wherein a concentration of the urea melt and the concentrated liquor stream that are conveyed to the urea granulator is between 95% wt. and 99.8% wt.

14. The method of claim 12, further comprising feeding a portion of the urea melt into the evaporation unit.

15. The method of claim 1, further comprising releasing the ammonia-reduced off-gas stream to the atmosphere, wherein the ammonia-reduced off-gas stream has a $NH_3$ concentration between about 5 $mg/Nm^3$ and about 30 $mg/Nm^3$.

* * * * *